United States Patent [19]
Frechet et al.

[11] Patent Number: 5,531,790
[45] Date of Patent: Jul. 2, 1996

[54] DEVICE FOR EXTENDING LIVING TISSUE

[75] Inventors: Patrick Frechet, 92, Avenue Mozart, 75016 Paris; Georges Fraisse, Saint Laurent du Var; Guy Charvin, Antibes, all of France

[73] Assignees: MXM, Antibes; Patrick Frechet, Paris, both of France

[21] Appl. No.: 244,508

[22] PCT Filed: May 7, 1993

[86] PCT No.: PCT/FR93/00441

§ 371 Date: May 27, 1994

§ 102(e) Date: May 27, 1994

[87] PCT Pub. No.: WO93/21849

PCT Pub. Date: Nov. 11, 1993

[30] Foreign Application Priority Data

May 7, 1992 [FR] France ................................ 92 05893

[51] Int. Cl.⁶ .................................................. A61F 2/10
[52] U.S. Cl. ............................ 623/15; 606/213; 606/215; 606/187
[58] Field of Search ........................... 606/204.35, 213, 606/215, 217, 218, 219, 220, 225, 187; 623/15

[56] References Cited

U.S. PATENT DOCUMENTS

| | | | |
|---|---|---|---|
| 679,993 | 8/1901 | Ross | 606/123 |
| 2,012,755 | 7/1934 | Muth | 606/217 |
| 2,421,193 | 8/1943 | Gardner | 606/215 |
| 2,472,009 | 8/1945 | Gardner | 606/216 |
| 2,575,205 | 11/1951 | Brown | 606/204.35 |
| 2,619,084 | 11/1952 | Brown | 606/204.35 |
| 2,669,747 | 2/1954 | Detaranto | 606/216 |
| 3,068,869 | 12/1962 | Shelden et al. | 606/216 |
| 3,473,528 | 4/1966 | Mishkin et al. | 606/57 |
| 4,007,743 | 2/1977 | Blake | 623/11 |
| 4,535,772 | 8/1985 | Sheehan | 606/217 |
| 4,976,726 | 12/1990 | Haverstock | 606/213 |
| 4,994,073 | 2/1991 | Green | 606/213 |
| 5,263,971 | 11/1993 | Hirshowitz et al. | 606/216 |

FOREIGN PATENT DOCUMENTS

| | | | |
|---|---|---|---|
| 0418970 | 12/1910 | France | 606/216 |
| 1412751 | 7/1988 | U.S.S.R. | 606/216 |

*Primary Examiner*—David H. Willse
*Assistant Examiner*—Bruce E. Snow
*Attorney, Agent, or Firm*—Dvorak and Traub

[57] ABSTRACT

A method and apparatus for extending living tissue. The apparatus being surgically implanted in the human body, and in particular beneath the scalp to extend hair producing tissue for reducing baldness. The apparatus includes at least one resilient means with at least two fastening means secured thereto. The fastening means are engageable with the living tissue and extend the tissue under the action of the resilient means. The apparatus is implantable, through a temporary opening, below the surface of the tissue to be extended, and extends the living tissue over a period of time, wherein the apparatus is later removed.

2 Claims, 6 Drawing Sheets

DEVICE FOR EXTENDING LIVING TISSUE

DESCRIPTION

The present invention relates to a device for extending living tissue.

The technical field of the invention is that of making materials that are surgically implantable in the human body.

One of the main applications of the invention is making extender devices that are implantable for a determined length of time beneath the scalp in order to diminish baldness, but other applications can be envisaged for the device of the invention wherever it is useful and/or necessary to stretch tissue, e.g. for diminishing wounds where it is necessary to be able to cover a damaged area with new skin, in particular when the original skin has been destroyed or damaged by burning, trauma, etc. . . .

With respect to so-called "male-pattern" baldness, it is known that definitive hair loss affects one in three of men aged 50.

Such baldness forms a part of a group of conditions known medically as "cicatricial alopecias": it is related to progressive and premature atrophy of hair follicles, at the roots of individual hairs, and its origins are genetic and hereditary.

So far, no medical treatment has managed to treat male-pattern baldness, and no therapeutic solution of a medical kind can be considered earlier than age 30 to 50.

At present, the only effective therapy is surgical, and more than 2 million Americans have had recourse to such surgery: this is done by surgically redistributing a fraction of healthy follicles that are genetically programmed to last throughout life. In practice, they constitute hair taken from around the tonsure.

For this purpose, essentially there are three techniques, namely: implants; reductions of the tonsure; and flaps; all three of which consist in moving healthy hair-carrying scalp to replace all or part of the bald scalp.

The present invention relates solely to the second and most recent technique of reducing tonsure: it makes it possible to achieve a clear improvement in results for extensive male-pattern baldness which constitute the major fraction of cases to be treated.

This technique consists in eliminating a region of bald skin and in moving towards each other the two edges of the wound once the surfaces situated beneath the scalp on either side of said wound have been separated. The two edges of the wound are then closed together under tension by means of surgical sutures stretching the scalp and thereby increasing the hair-carrying area at the expense of the bald area.

Thus, on average, it is possible to eliminate a 3 cm wide strip of bald scalp on each operation: four to six tonsure-reducing operations are then often required since there is a limit to skin resiliency and it is not reasonable to remove more than 3 cm at a time without running the risk of tearing; nevertheless, in spite of this high number of operations, and even if the number is increased, the result cannot be improved any further, and it is possible in this way to eliminate only about half of the initially bald area.

That failure to reduce the bald scalp area completely is related to two important phenomena that are combined:

There always occurs secondary distension or spreading of 20% to 50% of the bald areas close to the region of maximum tension, i.e. where the wound has been sutured, thereby generating a central region that always remains bald: this is well described and specified in the most important work on the topic devoted to surgery of the scalp, entitled "Hair transplantation", 2nd edition of 1987, by Mr. Rolf Norström and Walter Unger, in particular at pages 504 to 516, that specify area reductions in terms of percentages of the areas concerned by tonsure reduction.

A communication form Dr. Richard Shiell in Melbourne, Australia, dated February 1992, given during an international congress on scalp surgery at Los Angeles gives numerical results of the results of scalp reduction and confirms the limits of said technique.

Damage to or even final disappearance of ischemic hair follicles due to tension in the surface layers of the scalp, which disturbs and can slow down or even completely interrupt blood circulation, thereby giving rise to ischemia of said follicles.

Because of the two above phenomena, it is necessary to associate tonsure reduction operations with implants, thereby increasing both the cost and the overall duration of the procedure.

To eliminate the above phenomena, balloons placed beneath the hair-carrying scalp have been in use for about 10 years, particularly in America, with the balloons being inflated progressively at regular time intervals: the hair-carrying scalp is thus subjected to internal pressure and it expands and spreads. Once it is deemed to have expanded sufficiently, the operation can be performed as described above by removing a strip of the bald region, or even all of it, such that the lips of the remaining regions can be sewn together edge-to-edge, in the proper place.

It is thus possible to eliminate the entire bald area, replacing it with the hair-carrying regions that have been expanded by the balloons. Nevertheless, it is necessary to expand the balloons themselves regularly two or three times a week in order to achieve progressive expansion without tearing. This requires regular monitoring and, in any event, the resulting deformation of the head makes that technique unusable on a large scale. Any advantage in that technique is lost because of considerations and criteria relating to appearance and because of the difficulty in immobilizing people over long periods of time.

It usually takes several months to obtain a satisfactory result, and so for a fraction of that period the person concerned must remain isolated. In addition, there is always the danger of a balloon bursting and of the expansion regions being poorly monitored. These drawbacks give rise to a risk of further surgical intervention during treatment.

The above balloon technique is also common in other surgical treatments for the purpose of obtaining tissue expansion, whenever it is necessary to produce skin that is then used to cover a loss of substance in a patient, in particular for recovering regions that have been destroyed or damaged after burning or trauma.

One such device is described, for example, in French patent application FR 2 615 397 of May 20, 1987 filed by Marseille Assistance Publique for an "ambulatory device for continuous inflation at constant pressure of tissue-expansion balloons" and also in French patent application FR 2 608 916 of Dec. 26, 1986 filed by Messrs. Mai and Crassas for a "tissue expansion prosthesis". In both of those two patent applications, and as in many others throughout the world, there is described essentially a closed flexible body made of a biocompatible material that is suitable for expanding under the effect of fluid pressure and that is designed to be inserted beneath the tissue and/or skin to be repaired.

When the purpose is repair, the unattractive appearance of the balloons is of minor importance compared with the looked-for objective, even if the mobility and the comfort of the persons concerned is in any event limited, depending on the location where the balloons have been placed.

Thus, the problem posed is to be able to increase a given area of living tissue by a determined amount by lengthening it, taking advantage of the ability of cells to reproduce, while avoiding unattractive deformation of the volume of the portion of the body covered by said tissue, while limiting secondary stretching of the regions that it is not desired to stretch, and with a minimum number of surgical interventions over a period of time that is as short as possible.

A solution to the problem posed is a device for extending living tissue, comprising at least one resilient means whose outside dimensions in its active position enabling said tissue to be extended are such that a portion of its perimeter corresponds substantially to and is superposed with the edges of the area of tissue to be treated, and at least two fastening means each secured to a respective end of a resilient means of the device, which ends are opposite to each other in the direction of active resilience of said resilient means, and enable it to be fixed to said tissue along said edges.

In one embodiment, said resilient means may be a flexible part that is plane and of constant or varying thickness, made of an elastomer material of the silicone type.

In another embodiment, said resilient means may be constituted by an envelope made up of two hollow cylindrical portions that are open at least one end and that slide one within the other, a spring system being situated therein so as to enable it to be compressible while tending to move said portions apart towards a position of maximum separation that is limited by an abutment system, or else so as to be extensible and tending to move said portions towards each other.

The first embodiment thus serves essentially to apply traction on the ends and thus put regions of tissue situated outside the device under tension, even when they are far part from each other, whereas in the first type of the second embodiment, the traction effect is applied to the region of living tissue situated between its ends. One or other device is selected as a function of the type of intervention and of the looked-for objective. Other resilient means may also be developed for the application to reducing baldness constituting the main application described in the context of the present invention, and also as a function of other types of application, in particular closing up skin, or recovering regions that have been destroyed or damaged by accident.

The result is novel devices for extending living tissue, satisfying the various objects of the problem posed and responding to the various drawbacks mentioned above in existing systems, which systems are generally devices for expanding volume unlike those described in the context of the present invention which can be thought of as extension devices or "extenders", since they are concerned with selectively stretching a surface.

When extension devices of the present invention are used, the advantages of stretching living tissue such as hair-carrying scalp are obtained in the same manner as observed when using balloons, however in the present case the great advantage is associated with the fact that the stretching and progressive distortion of the tissue or of the hair-carrying scalp is not obtained by means of an increase in volume, and thus of an increase in area in all directions, but by an increase of surface area in given directions only. Thus, firstly there are no particular changes to the shape of the head, when the tissue is hair-carrying scalp, and secondly there is no stretching in directions that are not useful.

In addition, since the active ends of the extension device of the present invention can be placed exactly at the edges of the regions that are to be subjected to traction in order to change their surface area, regions that are not to be stretched are not subjected directly to said tension. Thus, in the context of stretching hair-carrying scalp, there is no secondary stretching of bald regions, thereby improving the efficiency of the system and the speed with which it acts. It is possible to apply traction to hair-carrying regions that are distant from the edges of the bald region, so that at the end of extension, and when the extender has returned to its rest position, said ends still being at a certain distance apart from each other, the distance between said ends corresponds to the combined width of the hair-carrying regions situated and held between the ends. A single operation then suffices to achieve the desired result. In addition, there is no destruction of follicles because of ischemia in the surface layers of the hair-carrying scalp, as can be observed in other techniques.

Compared with the basic technique of tonsure reduction, but avoiding the use of balloons for reasons of appearance, the number of surgical interventions is reduced to two, as is theoretically the case when using balloons, although there is the risk of intermediate interventions, namely one intervention for installing the device and another for removing it, and this is to be compared with the four to six interventions mentioned above.

Compared with the basic technique of reducing tonsure without balloons, it is also possible to emphasize that the overall duration of treatment is reduced since it is now no more than 1 to 3 months as compared with 12 months or more. This is due to the fact that during a single operation it is not possible to pull excessively on tissue that provides an initial resistance of more than 15 kg/cm$^2$, whereas by applying tension continuously and progressively, tissues adapt, regenerate, and thus lengthen in a manner that is relatively rapid.

Because of the reduced duration of treatment and the reduced number of surgical interventions, the overall cost of treatment is thus greatly reduced, as is the pain to which the person concerned is subjected, which person is all the more satisfied in that the bald area eliminated is much greater than it is when performing successive operations because of the absence of secondary stretching as mentioned above.

The extension device of the invention is also extremely simple, both as to its design and as to its handling in surgery, thereby making it a device that is highly advantageous, which is very compact being about 1 mm thick for flexible tissue, of constant thickness, but optionally being of varying thickness, and it is gently and smoothly "shapeable" to fit to any head.

It can thus be used for any case of extensive baldness, and also in all of the other applications mentioned above.

Further advantages of the present invention could also be mentioned, however those mentioned above already suffice to demonstrate the novelty and the advantage of the invention.

The following description and figures show embodiments of the invention but they are not limiting in any way: other embodiments are possible within the ambit of the scope and the extent of the present invention, in particular by changing the shape and the type of the resilient means, and also the shape and the type of the fastening means.

Figure 1A:
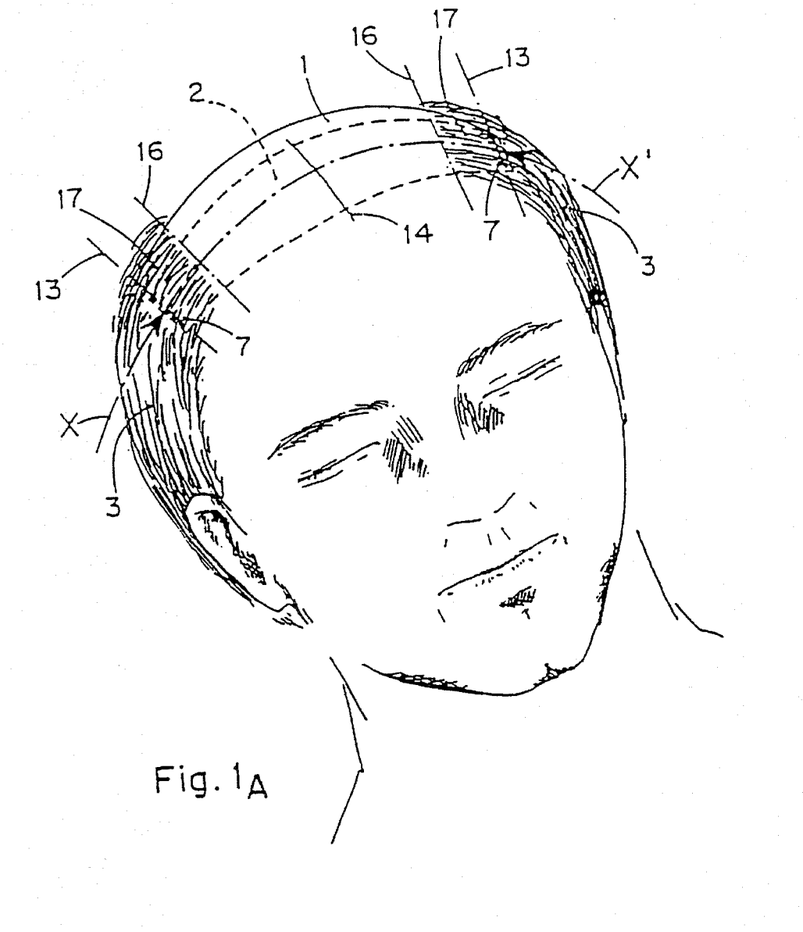
FIG. 1A is a diagrammatic perspective view of the device of the invention implanted on the head.

FIG. 1A is a diagrammatic perspective view of the head of a person whose scalp includes a bald region 1 and hair-carrying regions 3 situated at the periphery of said bald region 1.

The extension device 2 of the present invention is then disposed beneath said scalp, by incision of an opening 14 in the middle of said bald region 1. The fastening systems situated at the two opposite ends of the device 2 shown herein as being in the form of a rectangle as shown in FIG. 2A, and constituted by hooks 7, for example, are anchored in the galea 6 and in the hypoderma, that is to say the rigid fiber layer constituting the deepest portion of the scalp, shown in section in FIG. 1B.

Figure 3A:
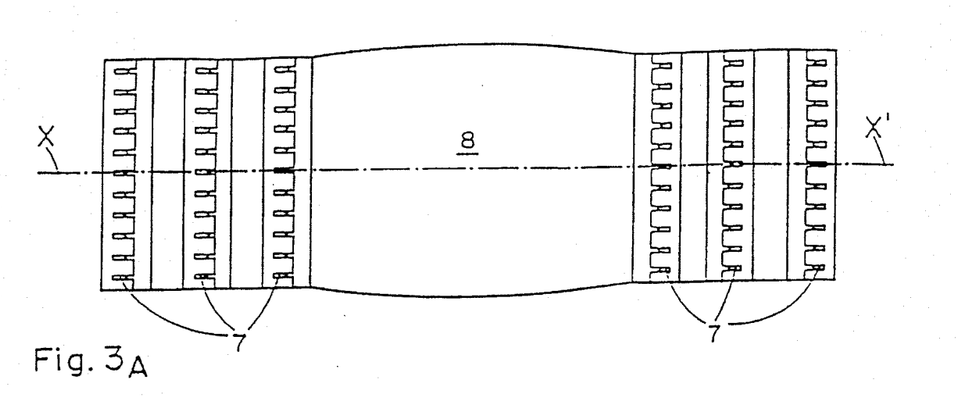
FIG. 3A is a plan view of another device implemented by combining resilient means.
Figure 3B:
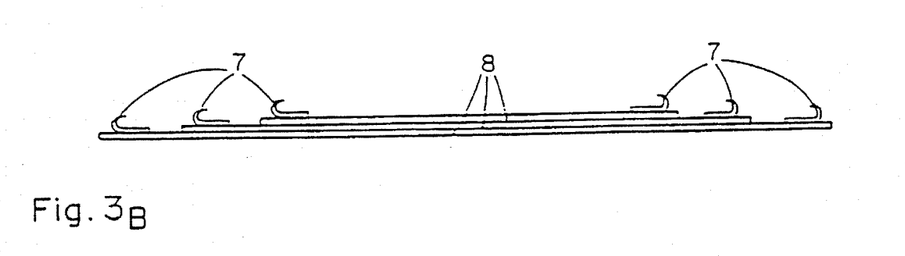
FIG. 3B is a side view of the FIG. 3A device.
Figure 3C:
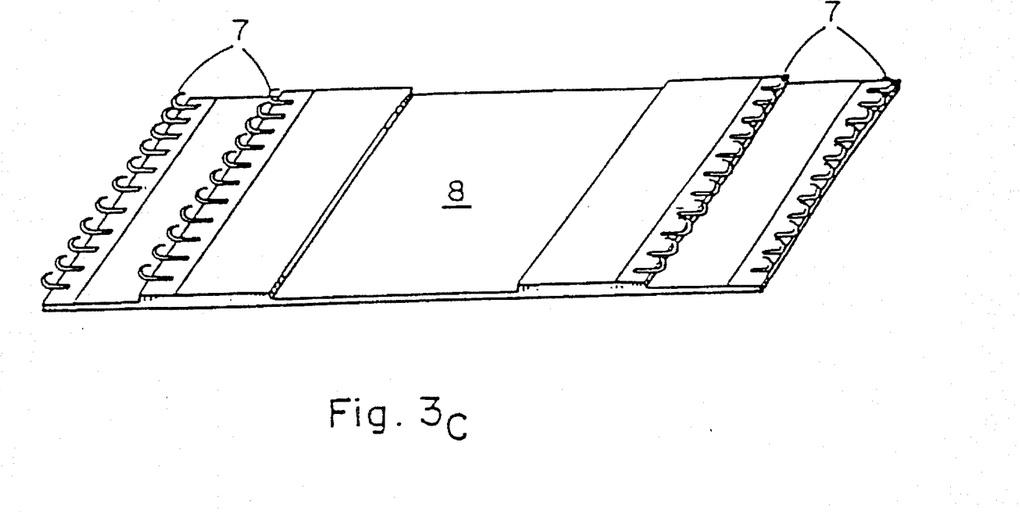
FIG. 3C is a side view of the device of FIGS. 3A and 3B, but shown in varying thickness.

Said fastening systems which may thus be installed along the edges 13 of a portion at least of the area of tissue to be treated, and in this case the example is the scalp where the purpose is to move the hair-carrying regions 3 towards each other. The edges 13 are not necessarily at the boundary 16 between the hair-carrying regions 3 and the bald region 1. It is preferable, as mentioned above, to apply traction to hair-carrying regions that are distant from the edges of the bald region so that at the end of extension and when the extender 2 has returned to its rest position, said ends still being at a certain distance apart from each other, the distance between said ends corresponds to the combined width of the hair-carrying regions 17 situated between the ends. This distribution of traction over the hair-carrying regions that are to be treated may be performed more completely and more effectively using the device shown in FIGS. 3.

Figure 5A:
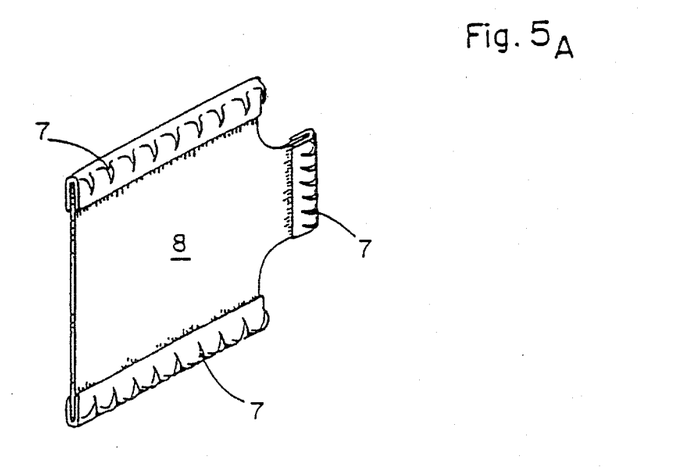
FIGS. 5A and 5B are two perspective views of two other embodiments of the device of the invention made of a flexible material.
Figure 5B:
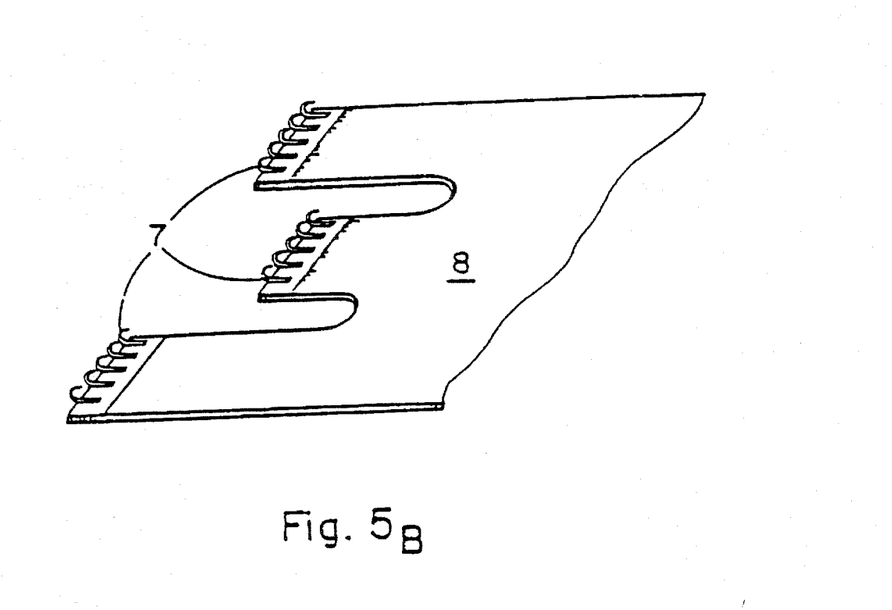

It is not necessarily useful or necessary to apply uniform and continuous force to the entire length of the edges 13 of the area to be treated, and traction and fastening may be applied to a portion only in nonadjacent regions thereof, depending on the state of the tissue and on the desired result, with this being made possible, for example, by an extension device of the kind shown in FIG. 5B. Adjacent regions lying between two points or two lines of traction are entrained indirectly to a greater or lesser extent depending on the disposition of the fastening systems 7, and in this way, even when applying traction only to a portion of the edges 13 of the region to be treated, the entire region will be subjected to the extension effect, but in a manner that is selective, determined, and defined, thus enabling the best possible desired result to be obtained.

Figure 4A:
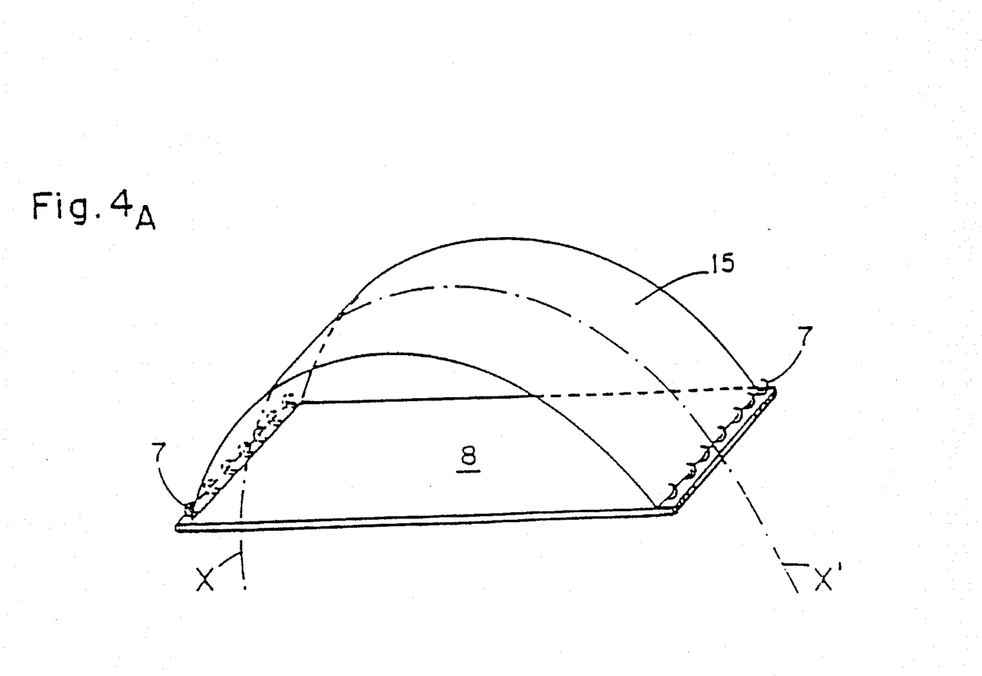
FIGS. 4A and 4B are perspective views of two embodiments of the device for installing the device of the invention.
Figure 4B:
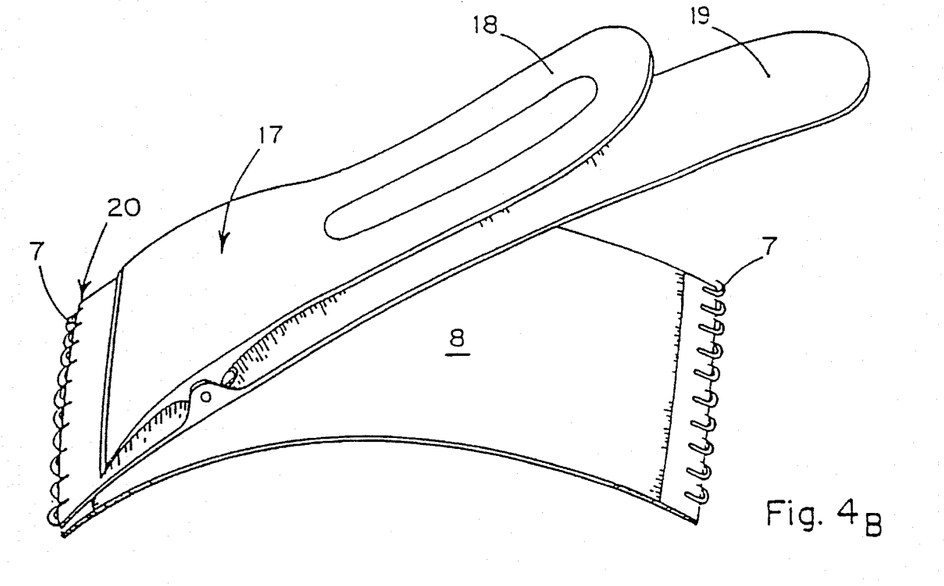

In the example of FIG. 1A, the extension device is a resilient device, also referred to as an extender, made of plane flexible parts of silicone type elastomer material, and it is put under tension while it is being installed by means of tools of the kind shown in FIGS. 4. Thereafter it contracts progressively in the direction of its active resiliency XX' in which force was initially applied, so as to return to its initial length, thereby moving its ends towards each other and thus also moving the fastening systems 7, thus tending to move said edges 13 towards each other while compressing the bald region 1 and, depending on circumstances, also compressing a fraction 17 of the hair-carrying regions situated between the fastening systems, as mentioned above. Confidential experiments have shown that such extension-compression takes place over a period of time that is of the order of 1 month to 2 months.

The scar 14 that enables the said device to be installed can then be reopened so that the device can be removed and so as to cut off the bald strip 1 which is then naturally in excess, after which the edges 16 can be sewn directly to each other.

The looked-for effect is thus obtained and no further surgical intervention is required. Throughout the entire duration of stretching and activity of the device, it remains invisible from the outside, and all that can be seen is a small amount of folding of the skin, which does not greatly change the appearance of the person who can therefore continue being active without being obliged to isolate himself from his environment as is the case with balloons.

Figure 1B:
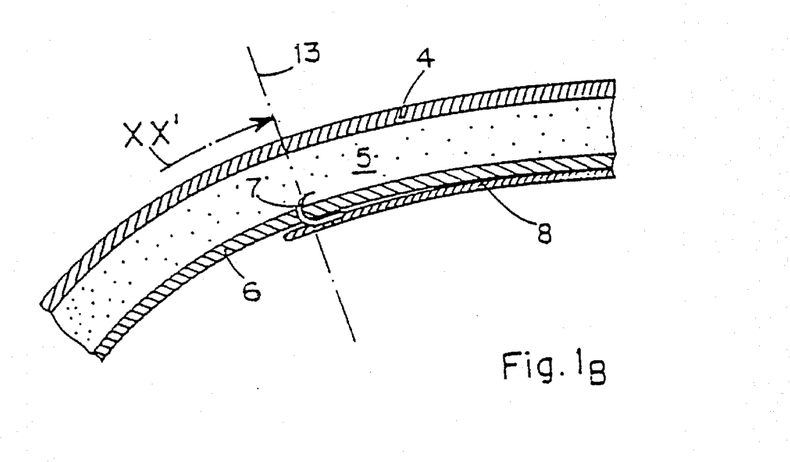
FIG. 1B is a fragmentary section view of the fastening of the device beneath the scalp.
Figure 2A:
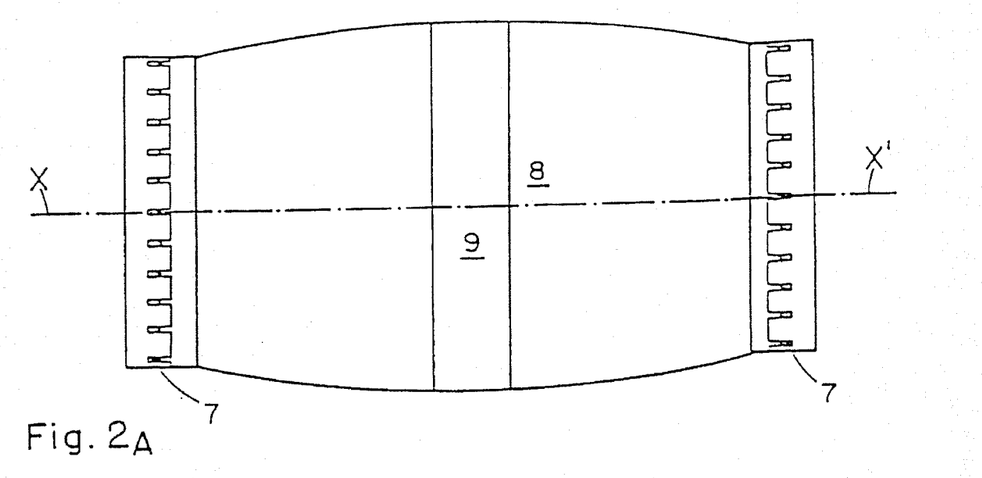
FIG. 2A is a plan view of an embodiment of the device.

FIG. 1B is a section view through the scalp in which the device of the invention has been anchored by one of its fastening systems 7 engaging in the galea and the hypoderma 6, i.e. the fibrous surface situated beneath the scalp 5 proper, itself protected by the outer skin 4. In the example of FIG. 1A, the fastening systems 7 tend to pull the edges 13 of the outer region to be treated 3 by applying traction thereto, whereas the region situated between said edges 13 is subjected, on the contrary, to compression.

Figures 6A, 6B:
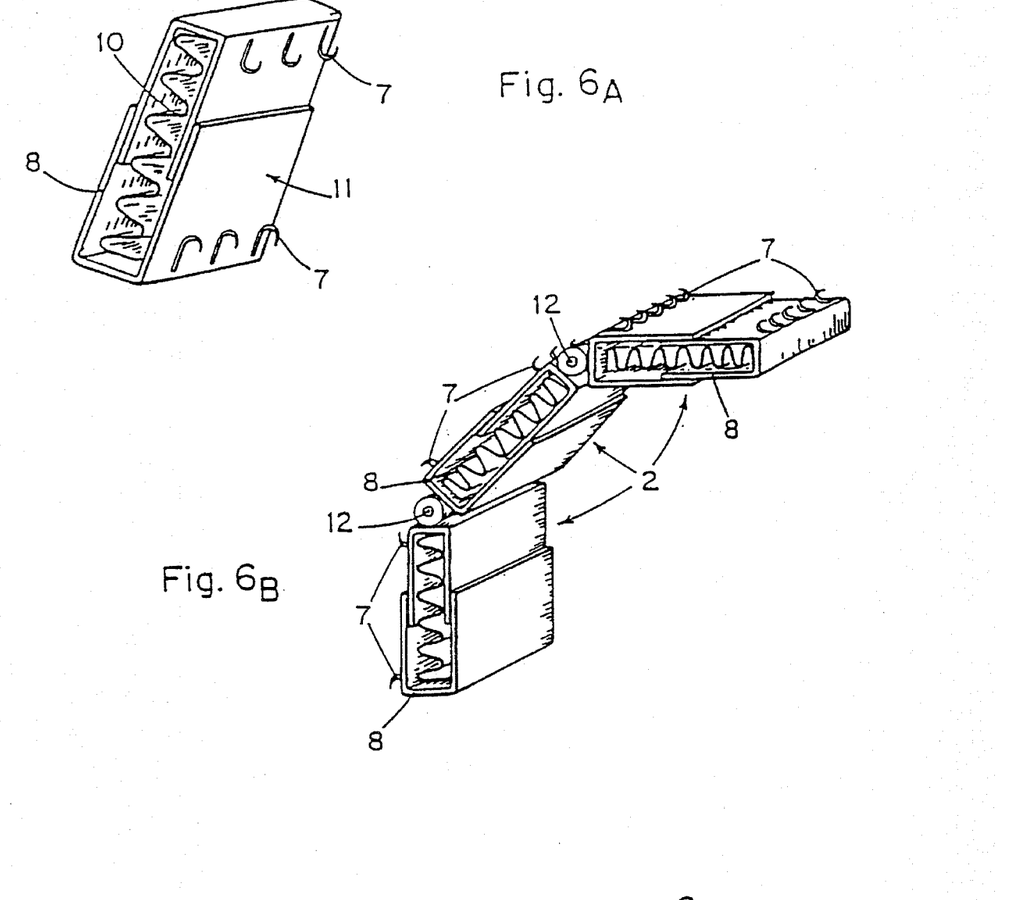
FIG. 6A is a perspective view of another embodiment of the device of the invention.
FIG. 6B shows a device made by hinging together devices as shown in FIG. 6A.

In the example of the device of the invention shown in FIGS. 6A and 6B, the fastening systems are situated in the opposite direction to the above, so as to provide fastening that makes it possible, on the contrary, to apply tension to the region situated between the fastening systems while applying compression to the regions situated outside them, with this being made possible by a compression spring 10 that tends to urge the fastening systems apart.

Figure 2B:
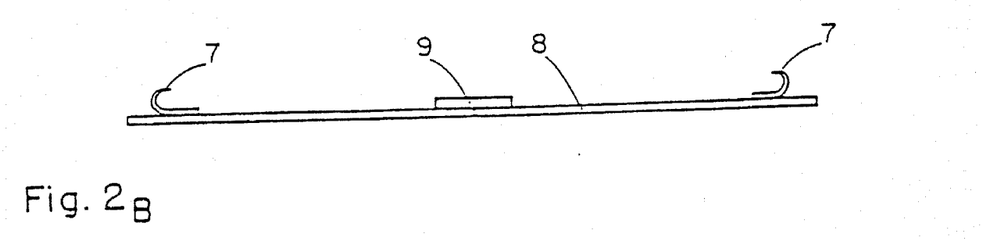
FIG. 2B is a side view of the FIG. 2A device.
Figure 2C:
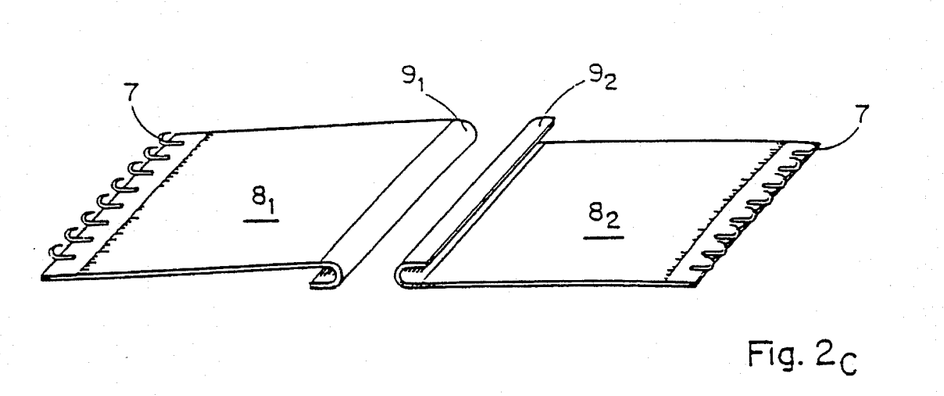
FIG. 2C is a perspective view of a two-part device having a central fastening.
Figure 2D:
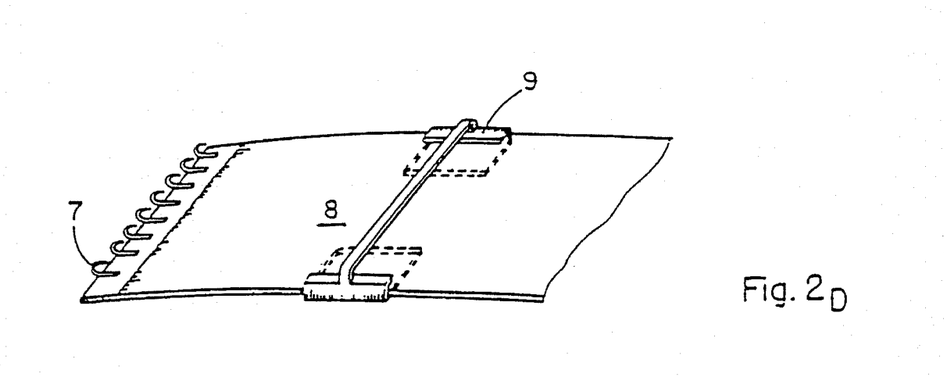
FIG. 2D is a perspective view of a device having a suture support.

FIG. 2A is a plan view of a device as implanted in the manner shown in FIG. 1A, in which said resilient means 8 is a flexible piece of silicone type elastomer material. FIG. 2B is a side view of such a device with said piece being flexible, plane, and of constant width and thickness, however it could also be of varying width and/or thickness as shown in FIGS. 3C and 3B, for example. In this figure, said piece is made of at least two separable portions each corresponding to and carrying one of said fastening means 7 at one end of the device, and said separable portions are united by an appropriate link means 9. Said link means may have three functions:

firstly, to enable the device to be installed in at least two mutually independent portions by hooking the end systems in the tissue to be treated and then by putting the two portions under tension end connecting them together by means of said device 9, without requiring the use of external means such as those shown in FIG. 4;

secondly, to be able to receive an adhesive or suture reinforcing system such as that shown in FIGS. 2B and 2D so as to enable the bald region 1 that is compressed by said device to be kept "glued" or sutured to the surface without any risk of large ugly folds being made that rise up under the effect of the compression; and finally, to be able to be made of a material that is stronger than the resilient piece 8 so as to make it possible during possible intermediate surgery to cut the scalp without running the risk of cutting said resilient piece, as shown in FIG. 2D. In this figure there can be seen reinforcement 9 for the suture that can be used even with a one-piece extender 8.

Said suture reinforcing or link piece 9 may be made of polyester type cloth or of metal-coated polyethylene plates, or of any other strong biocompatible material. It may either cover the two ends of the two portions in the middle of the extender 8, as shown in FIGS. 2A, 2B, or 2D, or else said link piece 9 may be made up of two elements each connected to one of the ends of said two portions of the extender, as shown in FIG. 2C so as to form a central fastening system.

FIGS. 3A and 3B constitute a plan view and a side view of another embodiment of the extension device of the present invention for extending living tissue, comprising a plurality of resilient means 8 of the above type constituted by independent plane superposable flexible pieces of constant or varying thickness and of different dimensions, with the largest piece being placed furthest from the surface of said tissue to be treated, the next largest piece being placed against the preceding piece, between it and the tissue to be treated, and so on up to the smallest piece which is thus directly in contact with said tissue over its entire area.

Such a device thus makes it possible to apply force along different lines of traction to a plurality of regions of tissue to be treated, thereby achieving better distribution of tensions and/or of different forces so as to obtain different amounts of tissue extension in different regions. Thus, when treating baldness, the hair-carrying regions 3 may have different densities of hair, and it is thus possible to make hair density more uniform.

For the same purpose, the plane flexible pieces constituting said devices may be made of varying widths and thicknesses, so as to apply more or less force to various regions of the living tissue. This makes it possible to have either a single resilient flexible piece on which fastening systems 7 can be secured in different locations, as shown in FIG. 3C, without any need for superposed layers of pieces as shown in FIGS. 3A and 3B, or when using such superposed layers as shown in FIGS. 3A and 3B, to obtain complex selective stretching effects. This is in addition to and combined with the possibility of disposing fastening systems at selected points in a continuous line as shown in FIGS. 2 and 3, or in a discontinuous line as shown in FIGS. 5, all along the edges 13 of the region to be treated or over a portion only thereof, as mentioned above and below.

FIGS. 4A and 4B are perspective views of two examples of tools for installing the extension device constituted by resilient means 8.

In FIG. 4A, it is shown in the rest position prior to being extended and shaped, e.g. to the shape of a head, by means of an installation tool 15. It is pressed against the portion of the body whose shape is to be taken up by the resilient piece 8 by elastic deformation thereof under traction, until said fastening systems 7 reach the edges 13 of the area of tissue to be treated and are hooked thereto, thereby enabling said tool 15 to be withdrawn. However the tool is not necessary when said flexible piece is made up of two mutually separable portions as shown in FIGS. 2A and 2B.

FIG. 4B shows another tool 17 suitable for installing the fastening systems 7 one after the other. It comprises a tip 20 for engaging in said hooks or fastening systems 7, like the tool in FIG. 4A, which tip is at the end of a handle 19, and it includes a hinged lever 18 whose shape makes it possible to detach the scalp or other living tissue beneath which said extender 8 is to be slid, with this being done by pressing the lever against said handle 19 of the tool. Thus, this tool serves not only to install the extender, but also makes it possible to remove it in a manner that is relatively simple and practical.

FIGS. 5 show other examples of devices of the invention in which said resilient means 8 include three fastening means 7. In FIG. 5A, two of the fastening means 7 are situated in opposite directions to each other as in the preceding figures, while the third fastening means extends along a perpendicular direction, thus making it possible, for example, also to pull in a hair-carrying region from the back of the scalp, should that be necessary. In FIG. 5B, the three fastening means 7 shown in fact constitute a single fastening means 7 according to the preceding definition, situated on one side only of a single end of the resilient means 8, however the fastening means extend along lines that are not continuous relative to one another, thereby causing certain regions to be subjected to greater force than others, it being understood that the intermediate regions are subjected to indirect force as explained above.

Figure 7:
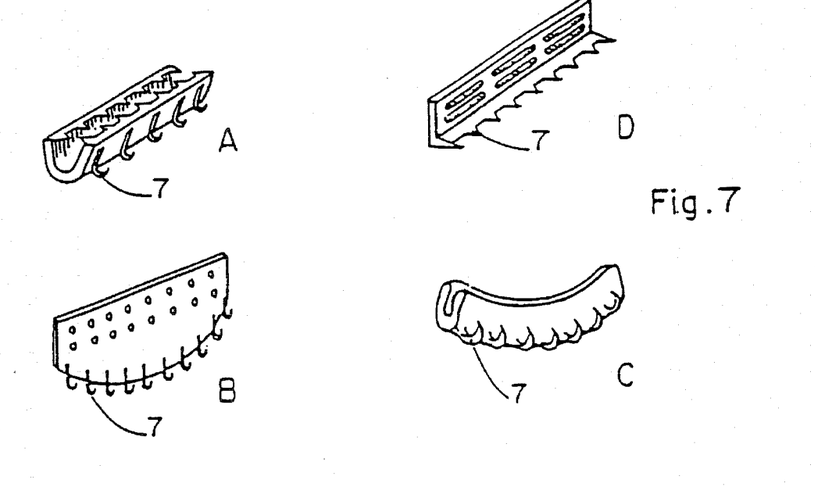
FIG. 7 shows various other embodiments of the fastening system.

It is also possible to make other devices with four, five or even more fastening devices depending on the desired objective, said devices 7 possibly following straight lines as shown in FIGS. 1 to 6 and 7A and 7D, however they could also follow curved lines as shown in FIGS. 7B and 7C, or they could have any other continuous or discontinuous line shape as mentioned above, depending on the regions that are to be subjected to traction relative to the entire region to be treated, as a function of the looked-for result and of the initial situation.

FIGS. 6A and 6B show another embodiment of the device of the invention in which said resilient means 8 is constituted by an envelope 11 made up of two mutually slidable, semi-closed portions containing an appropriate spring system 10 that is either compressible, tending to move apart said portions to a position of maximum separation that is defined by some appropriate abutment system, or else is extensible tending to move said portions towards each other. In the first type, the fastening systems 7 are directed outwardly relative to the device, as shown in FIG. 6A, whereas in the second type they are directed inwardly as shown in FIGS. 1 to 5. In FIG. 6B, the device of the invention comprises a plurality of envelopes 11 that are hinged to one another about axes 12 enabling the set of said envelopes 11 to be fitted over the natural shape of the living tissue to be treated.

FIG. 7 shows a plurality of embodiments of the fastening system 7, which system may be constituted by hooks, claws, clamps, or any other linking means capable of anchoring in living tissue and transmitting the tension of the resilient means 8, and having a system suitable for connecting them to said resilient means in the particular configuration thereof, e.g. by clamping, by welding, by sewing, by snap-fastening, etc. . . .

Devices of the invention may also be implanted externally, under the condition that when reducing baldness as in the above-specified application, the hooks are placed in the galea itself, passing through the entire thickness of the scalp so as to cause it to move and obtain the looked-for result, even though appearance will not be good given that the device of the invention can be seen from the outside, however it may possibly be camouflaged by a portable wig while such compression traction is taking place since there is no change in volume per se, and there is no need to perform a surgical operation to install the device.

In other applications, devices of the invention can be used whenever there is a need to tension or stretch the area of a tissue that is strong enough to avoid tears or breaks of the fibers, and whenever said stretching of tissue is desirable.

What is claimed is:

1. A device for extending living tissue having a deep fibrous layer, the device surgically implantable under the living tissue, the device comprising at least one resilient means and at least two fastening means, each fastening means coupled to a respective end of the resilient means, whose outside dimensions, in its active position, are such that a portion of its perimeter corresponds substantially to and is supported with edges of an area of tissue to be treated, wherein said resilient means is constituted by an envelope made up of two hollow cylindrical pieces that are open at least one end that slide one in the other, a compressible spring system being placed therein and tending to move said pieces apart to a position of maximum separation limited by an abutment system, the fastening means being fixable to the rigid fibrous layer near the edges of the tissue, which ends of the resilient means are opposite to each other in the direction of active resilience of said resilient means.

2. The extension device for living tissue according to claim 1, wherein the device is made up of a plurality of envelopes that are hinged to one another about axes enabling said envelopes to follow a natural shape of the living tissue to be treated.

* * * * *